United States Patent [19]
Wolff

[11] Patent Number: 5,104,404
[45] Date of Patent: Apr. 14, 1992

[54] ARTICULATED STENT

[75] Inventor: Rodney G. Wolff, Maple Grove, Minn.

[73] Assignee: Medtronic, Inc., Minneapolis, Minn.

[21] Appl. No.: 721,914

[22] Filed: Jun. 20, 1991

Related U.S. Application Data

[63] Continuation of Ser. No. 416,000, Oct. 2, 1990, abandoned.

[51] Int. Cl.$^5$ ............................................. A61F 29/00
[52] U.S. Cl. ....................................................... 623/1
[58] Field of Search .................... 623/1, 2, 11, 12, 66; 606/191, 198

[56]          References Cited
       U.S. PATENT DOCUMENTS

| | | | |
|---|---|---|---|
| 4,503,569 | 3/1985 | Dotter | 128/303 |
| 4,553,545 | 11/1985 | Maass et al. | 128/341 |
| 4,580,568 | 4/1986 | Gianturco | 128/348 |
| 4,649,922 | 3/1987 | Wiktor | 128/344 |
| 4,830,003 | 5/1989 | Wolff et al. | 128/343 |
| 4,856,516 | 8/1989 | Hillstead | 623/1 |

OTHER PUBLICATIONS

Schatz, R. A.; "A View of Vascular Stents" Circulation 1989; vol. 79, No. 2, Feb. 1989.
Schatz, R. A.; Dalmaz, J. C.; TiO, F.; Garcia, O.; Report of a New Articulated Balloon Expandable Intravascular Stent (ABEIS) Circulation, 1988; vol. 78 (Suppl. II): II-449.
Palmaz, et al, Expandable Intraluminal Vascular Graft: A Feasibility Study, Feb. 1986, Surgery, pp. 199-205.
Palmaz, et al, Expandable Intraluminal Graft: A Preliminary Study, 1985, Radiology, pp. 73-77.
Palmaz, et al, Atherosclerotic Rabbit Aortas: Expandable Intraluminal Grafting, 1985, Radiology, pp. 723-726.

*Primary Examiner*—David Isabella
*Attorney, Agent, or Firm*—Harold R. Patton

[57]          ABSTRACT

In a first embodiment a number of stent segments are connected together by hinges welded in place to provide articulation between the stent segments. The hinges can be, among other shapes, either a straight wire or a coiled wire of biocompatable material. A second embodiment uses a stent of a previous invention made up of a number or wires welded together for the stent segments with connection between adjacent stents provided by having one of the wires of adjacent stents continue between these adjacent stents to provide a hinge action. In this embodiment the wire portion extending between the segments is ground to a smaller diameter than the wire of the stent segment itself, to provide the necessary hinge flexibility. This articulated stent, made up of a number of individual stent segments, gives support for curved arteries, with the hinges between the segments providing both articulation and spacing between the stent segments. This articulated stent is tailored to match the curvature existing in the artery and is positioned at the site with the necessary preferred angular orientation using a previous catheter system.

19 Claims, 3 Drawing Sheets

ARTICULATED STENT

This is a continuation of copending application Ser. No. 07/416,000 filed on Oct. 2, 1990, now abandoned.

FIELD OF THE INVENTION

The present invention relates to intravascular stents which are applied within the peripheral or coronary arteries of a living animal or human being to maintain patency after a balloon angioplasty, either a percutaneous transluminal coronary angioplasty (PTCA) or a percutaneous transluminal angioplasty (PTA) procedure. This invention relates particularly to arteries which have a curved portion, curved and recurved portions, changes in diameter, which are difficult to obtain using existing stents; and also to extend the length of coverage provided by a single stent which can be installed during a single procedure.

BACKGROUND OF THE INVENTION

The advantage of utilizing a stent in conjunction with a PTCA or PTA procedure is well known. Earlier stents required an expansion procedure to expand the stent to provide support for the blood vessel after implantation. Later improvements including U.S. Pat. No. 4,830,003 regarding a Compressive Stent and Delivery System, Rodney G. Wolff et al co-invented by me, utilized a catheter system to hold a spring loaded stent compressed and to place the stent at the desired location within an artery. This approach greatly improved the utility of the stent and minimized previous problems, but required the use of multiple stents to provide support where a blood vessel curved to any extent and for extended lengths. While such an approach is possible the difficulty of spacing separate adjoining stents accurately and possible interference between these adjacent stents can reduce their effectiveness and will always increase the procedure time.

SUMMARY OF THE INVENTION

The problems associated with the use of multiple stents in curved arteries, or arteries having a change in size such as at a branch, led to my developing the instant device. This device utilizes a number of stent segments flexibly connected together by a hinge between each adjacent stent segment. This approach not only allows use of unequal diameter stent segments as the artery diameter changes, and permits articulation between adjacent stent segments, but also maintains the spacing between adjacent segments as established by the hinge lengths. In a first embodiment my prior co-invention, which utilizes a stent made up of a number of individual wires welded into a tubular shaped structure for the stent segments, is incorporated as an example. This use of my previous stent is merely illustrative here as any metal stent segments can be connected together using a metal hinge welded between adjoining stent segments. A relatively small number of stent segments are shown in the example but as many segments as may be required can be attached together using this approach. When the stent is located within an artery which has a bend, the hinges are preferably located on the outside of the bend. This permits the hinge to provide additional support between stent segments on the outside of the bend and also permits the inside edge of the stent to close to provide additional support on that side. It follows that where an artery curves in only one direction, all of the hinges will be located on one side. In cases where an artery curves first in one direction and then in the opposite direction however, the first hinge will be located on one side and the second hinge on the opposite side to provide the required matching stent articulation. Likewise any other angular relationship can be accommodated by the appropriate location of the hinges in relation to the stent circumference of adjacent stent segments.

For all applications the artery size and shape is measured first to determine the number of stent segments, their respective diameters, lengths, stent segment spacing, and the support required of each respective stent segment. The hinge characteristics as to length, strength and location on the stent circumference are also determined from these measurements. An articulated stent is then manufactured to conform to this specific artery by incorporating all of the respective stent and hinge requirements into this stent. The catheter system of my previous co-invention is also utilized here to deliver this articulated stent to the arterial site with the proper orientation. The hinges are made either of radiopaque material or are coated with radiopaque material to permit observation of the angular orientation of the stent relative to the blood vessel. Rotating the appropriate catheter will rotate the articulated stent to the correct orientation aided by simultaneously observing the results on a fluoroscope during the rotation. This rotation is accomplished after the stent is positioned at the site. The prior site positioning and placement using this previous catheter system are employed essentially the same here as for my previous single segment stent.

The hinge used can be simply a wire welded between adjacent stent segments. Where additional flexibility for a given hinge strength is needed, the wire hinge can be coiled along its length in a manner similar to a coiled lamp filament. This approach retains the strength of a particular wire size but provides much greater flexibility between stent segments. Any other metal shape having the necessary hinge characteristics can be used for this hinge segment however.

While this hinge works well with my previously co-invented wire stent there is no limitation in this approach which requires that it be used with only my stent. Further, any kind of metallic stent can be welded to a metal hinge by using either laser or resistance welding.

A second embodiment, which requires the use of my previous stent, provides the hinges by extending one of the wires making up adjacent stent segments continuously both through the stents and also through the gap between them. This continuous wire is normally not the same gage between the stent segments as the wires in the stent segments themselves. This wire is usually ground to a smaller diameter in the spaces between the stents to provide additional flexibility for the hinge function. This continuous wire provides the necessary hinge action between the stent segments rather than welding a separate hinge in place.

As before, when an artery is curved in one direction only, the continuous wire can extend through and between all stent segments. When the artery curves change direction, then the continuous wires preferably extend only through contiguous segments which are bent in the same direction. For example, where a first bend in one direction is followed by a second bend in an opposite direction, a first continuous wire will extend only through a first and second segment and the gap between them on one side of the articulated stent, and a second continuous wire will extend only through the second and a third segment and the gap between them on the opposite side. This change in direction is accommodated by this change in the location of the continuous wire which extends between subsequent stent segments relative to the stent circumference. Any change in direction of subsequent bends can be accommodated by extending the wire on the appropriate side between segments.

DETAILED DESCRIPTION OF THE PREFERRED EMBODIMENTS

Figure 1:
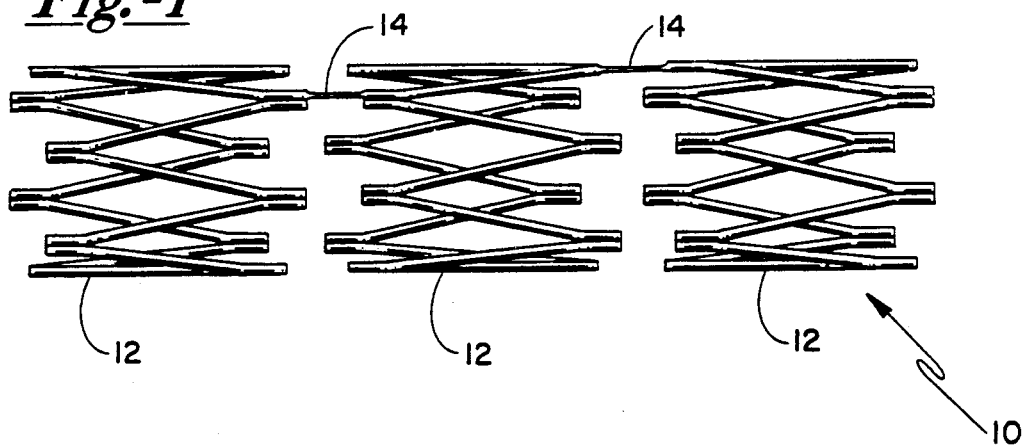
FIG. 1 shows an articulated stent of three stent segments connected together by two wire hinges welded to the same side of the segments.
Figure 2:
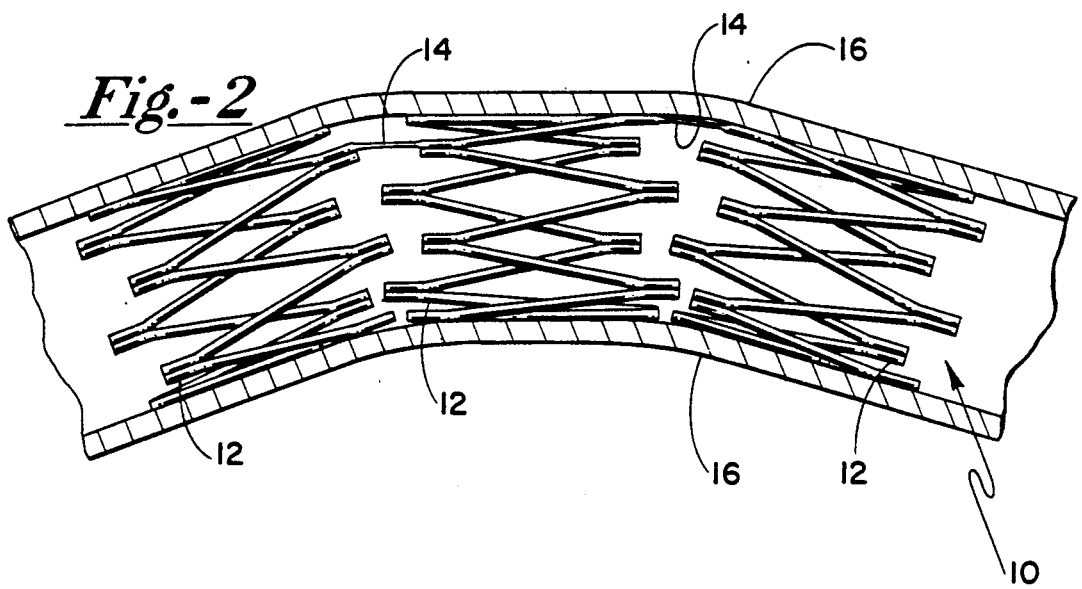
FIG. 2 shows the articulated stent of FIG. 1 in situ in an artery which has a bend in one direction only.

In FIG. 1 an articulated stent 10 is shown with three stent segments 12 and two interconnecting hinges 14. Stent segments 12 are each made of individual wire elements welded together, as described in my previous co-invention. Hinges 14 are made of biocompatable spring material and are of a smaller diameter than those used in forming stent segments 12. Hinges 14 are welded at each end to stent segments 12 using either laser or resistance welding techniques. Hinges 14 ar both attached to the same side of stent segments 12. This is because stent 10, shown in FIG. 1, is installed in artery 16, as shown in FIG. 2 which bends in one direction only. Hinges 14 are all located on the outside of the bend with the inner edges of stent segments 12 closer together because of the bend. This hinge location for the hinges accomplishes two purposes. First, hinges 14 act as a bridge between adjacent stent segments 12 to provide additional support for the artery. Second, since the edges of stent segments 12 on the side opposite to hinges 14 are bent toward each other, having the hinge spacing located on the outside portion of the articulated stent 10 allows these inner edges to close. This also provides additional arterial support on this inside edge. These hinges, as discussed earlier, can either be made of radiopaque material or can be coated with radiopaque material to permit determining the orientation of the articulated stent within an artery using a fluoroscope.

Figure 7:
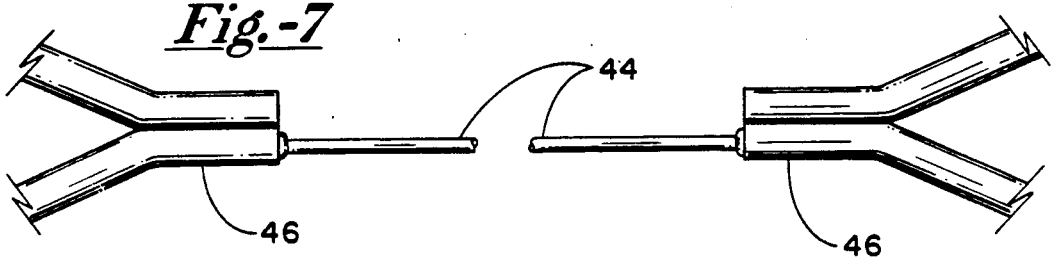
FIG. 7 is a detail of a hinge welded to the end of two adjacent stent segments.
Figure 8:
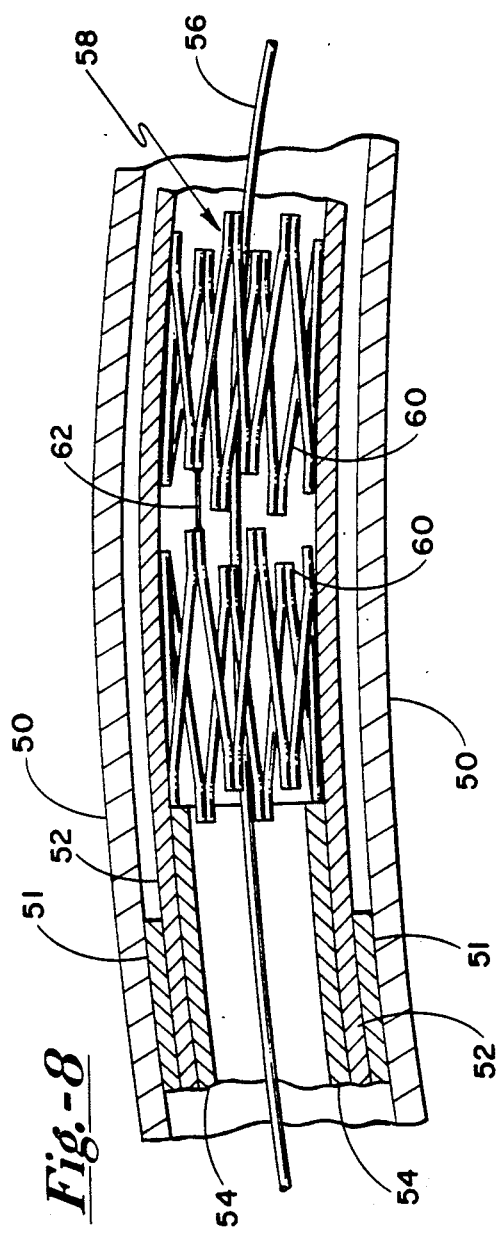
FIG. 8 is a detail of the stent delivery system of my previous co-invention in an artery in cross-section, holding an articulated stent.
Figure 9:
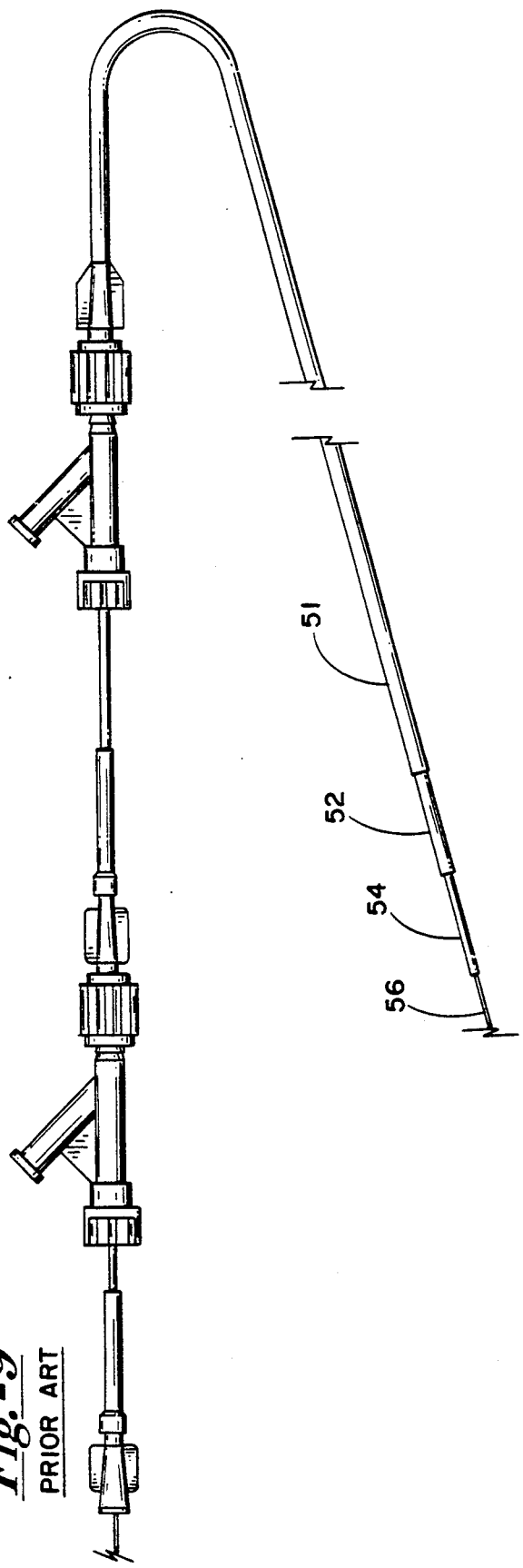
FIG. 9 shows the catheters and guide wires of my previous co-invention delivery system.

In use, the articulated stent is delivered to the site using the same delivery scheme as for my previous co-invention as shown in FIGS. 7 and 8; having a guide catheter 51, an outer catheter 52 to compress and position the stent within the blood vessel, an inner catheter 54 to hold the stent at the desired site while the outer catheter is removed to deposit the stent in situ and an optional guide wire 56. If the stent orientation is incorrect, the outer catheter 52 is rotated within the guide catheter 51 to obtain the desired orientation while observing the results on a fluoroscope screen.

Figure 3:
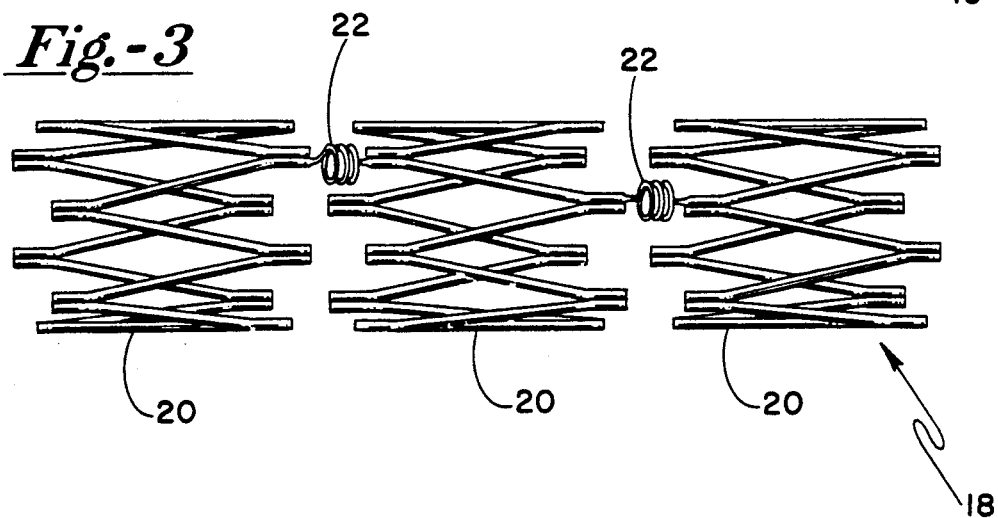
FIG. 3 shows an articulated stent of three wire segments connected together by two coiled wire hinges welded in place.

In FIG. 3 articulated stent 18 is made up of three stent segments 20 which are connected together by two coiled hinges 22 consisting of a wire coiled about its length. Hinge 22 is also welded at each end to a wire of the adjacent stent segment 20. As discussed previously, coiling the wire making up hinge 22 increases the bending flexibility of the wire while retaining the strength.

Figure 4:
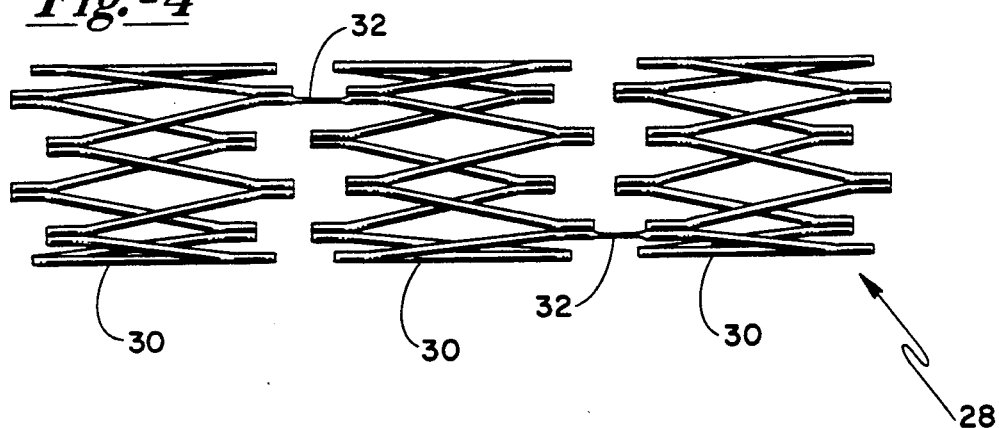
FIG. 4 shows an articulated stent of three stent segments connected together by two wires extending between and through the opposite sides of adjoining stent segments.
Figure 5:
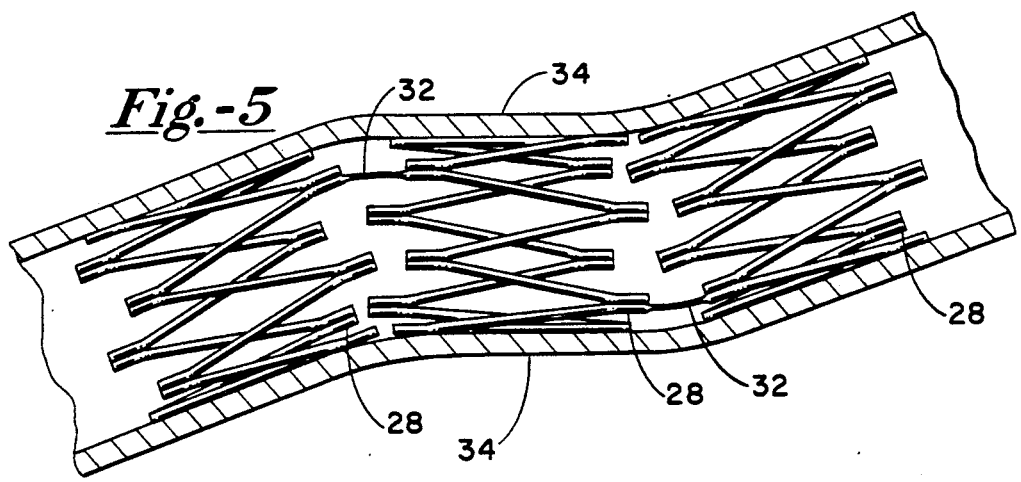
FIG. 5 shows the articulated stent of FIG. 4 in situ in an artery shown in cross-section which has bends in two directions.

In FIG. 4 an articulated stent 28 is made up of three stent segments 30 connected together by two wires 32 which extend through and are a part of the respective adjoining segments. Wires 32 are located generally on opposite sides of the articulated stent and each wire is welded to and made a part of the the adjacent stent segments 30. The diameter of wires 3 between adjacent stent segments 30 is reduced by a grinding process to provide additional flexibility in this hinge region. This opposed arrangement of wires 32, which effectively form the hinges is used when a bend and a reverse bend are adjacent to each other in an artery which must be supported by an articulated stent, since the hinges are preferably located on the outside of the bends. In FIG. 5 articulated stent 28 of FIG. 4 is installed within an artery 34 which has such a bend and a reverse bend.

Figure 6:
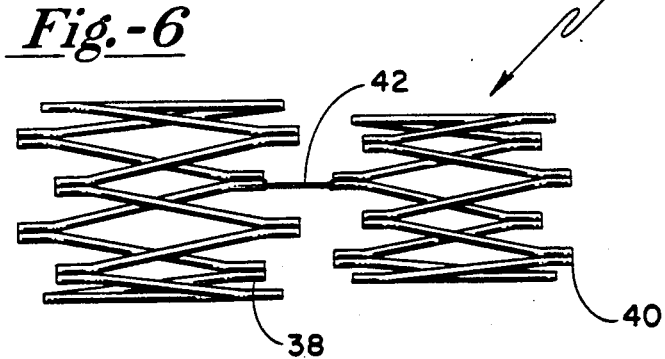
FIG. 6 shows an articulated stent with segments of unequal size joined by a welded wire hinge.

In FIG. 6 an articulated stent is shown with a stent segment 38 which is larger than another stent segment 36 which are connected by a hinge 42. This illustrates how a change in diameter of an artery can be accommodated.

In FIG. 7 a detail of a wire hinge 44 welded to the ends of two adjacent stent segments 46 is shown. A wire or any other metal segment having equivalent flexibility can be used to connect adjacent metal stent segments together to provide the necessary function.

The articulated stents shown here are only representative of some of a great number of possible combinations of stent segments. Further, any other metal stent segments which are taught elsewhere including dissimilar types of stent segments, can be attached together using the biocompatable metal hinges of this invention, by merely welding the hinges in place. The hinges can be of any type, length, or diameter.

The fact that this articulated stent can be tailored for the requirements of any arterial site is the essence of this invention. The artery to be supported is mapped prior to a PTCA or PTA procedure to determine the required diameter, support, and spacing of each stent segment and the flexibility and length of each hinge. An articulated stent is then manufactured taking all of these requirements into account. After the PTCA or PTA procedure, while the guide catheter is still in place, the outer catheter, inner catheter, articulated stent and guide wire are then placed within the guide catheter to position the articulated stent in situ.

While this invention has been described with reference to illustrative embodiments, these descriptions are not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

What is claimed is:

1. An articulated separate stent comprising:
    at least two stent segments, each stent segment having a generally tubular shape; and
    a hinge means extending between and connecting adjoining stent segments whereby the stent segments may flex and articulate about said hinge means to provide support for curved blood vessels.

2. An articulated stent according to claim 1 wherein the stent segments are formed from a plurality of wires.

3. An articulated stent according to claim 1 wherein the hinge means includes radiopaque material.

4. An articulated stent according to claim 1 wherein the hinge means is comprised of flexible wire.

5. An articulated stent comprising:
    at least two separate stent segments, each stent segment formed from a plurality of wires into a generally tubular shape; and
    hinge means extending between connecting adjoining stent segments whereby the stent segments may flex and articulate about said hinge means to provide support for curved blood vessels.

6. An articulated stent according to claim 5 wherein the wires of the stent segments are comprised of biocompatable metal.

7. An articulated stent according to claim 5 wherein the stent segment wires extend substantially the length of the stent segment and are joined together into a tubular unit.

8. An articulated stent according to claim 7 wherein the hinge means is a single wire common to two adjacent stent segments.

9. An articulated stent according to claim 8 wherein the single wire is a coiled wire.

10. An articulated stent according to claim 7 wherein the single wire is comprised of radiopaque material.

11. An articulated stent comprising:
    at least two separate stent segments, each stent segment formed from a plurality of wires into a generally tubular shape; and
    a single, flexible wire extending between and connecting two adjacent stent segments whereby the stent segments may flex and articulate about said flexible wire to provide support for curved blood vessels.

12. An articulated stent according to claim 11 wherein the single, flexible wire is a coiled wire.

13. An articulated stent according to claim 1 wherein the single, flexible wire is comprised of radiopaque material.

14. An articulated stent for placement in a lumen of a body organ comprising:
    first and second separate stent segments, each stent segment having structure for maintaining patency of the lumen; and
    hinge means extending between and connecting the first and second stent segments flex and whereby the stent segments articulate about said hinge means to allow the segments to independently act on the lumen.

15. An articulated stent according to claim 14 wherein the first and second stent segments are comprised of a plurality of wires formed into a generally tubular shape.

16. An articulated stent according to claim 15 wherein the stent segment wires extend substantially the length of the stent segment and are joined together into a tubular unit.

17. An articulated stent according to claim 14 wherein the hinge means is a single wire common to each of the first and second stent segments.

18. An articulated stent according to claim 17 wherein the single wire is a coiled wire.

19. An articulated stent according to claim 14 wherein the hinge means includes radiopaque material.

* * * * *

UNITED STATES PATENT AND TRADEMARK OFFICE
CERTIFICATE OF CORRECTION

PATENT NO. : 5,104,404
DATED : April 14, 1992
INVENTOR(S) : Rodney G. Wolff

It is certified that error appears in the above-indentified patent and that said Letters Patent is hereby corrected as shown below:

Column 5, line 5, delete "separate".

Column 5, line 6, insert --separate-- between the words "two" and "stent".

Column 5, line 23, insert --and-- between the words "between" and "connecting".

Column 6, line 21, before "flex and".

Column 6, lines 22, insert --flex and -- after "segments".

Signed and Sealed this

Thirteenth Day of February, 1996

Attest:

BRUCE LEHMAN

*Attesting Officer*  *Commissioner of Patents and Trademarks*

Adverse Decisions In Interference

Patent No. 5,104,404, Rodney G. Wolff, ARTICULATED STENT, Interference No. 103,432, final judgment adverse to the patentee rendered April 20, 1998, as to claims 1-8, 10, 11, 13-17, and 19.
*(Official Gazette July 7, 1998)*